US009924917B2

(12) United States Patent
Tsubota et al.

(10) Patent No.: US 9,924,917 B2
(45) Date of Patent: Mar. 27, 2018

(54) X-RAY CT DEVICE AND PROCESSING METHOD

(71) Applicant: Hitachi, Ltd., Tokyo (JP)

(72) Inventors: Yushi Tsubota, Tokyo (JP); Fumito Watanabe, Tokyo (JP); Yasutaka Konno, Tokyo (JP); Shinichi Kojima, Tokyo (JP); Keisuke Yamakawa, Tokyo (JP)

(73) Assignee: Hitachi, Ltd., Tokyo (JP)

(*) Notice: Subject to any disclaimer, the term of this patent is extended or adjusted under 35 U.S.C. 154(b) by 195 days.

(21) Appl. No.: 14/889,634

(22) PCT Filed: May 2, 2014

(86) PCT No.: PCT/JP2014/062134
§ 371 (c)(1),
(2) Date: Nov. 6, 2015

(87) PCT Pub. No.: WO2014/188864
PCT Pub. Date: Nov. 27, 2014

(65) Prior Publication Data
US 2016/0081643 A1 Mar. 24, 2016

(30) Foreign Application Priority Data

May 24, 2013 (JP) ................................ 2013-109995

(51) Int. Cl.
*G06T 7/00* (2017.01)
*A61B 6/00* (2006.01)
(Continued)

(52) U.S. Cl.
CPC .............. *A61B 6/482* (2013.01); *A61B 6/032* (2013.01); *A61B 6/461* (2013.01); *A61B 6/467* (2013.01);
(Continued)

(58) Field of Classification Search
CPC ......... A61B 6/482; A61B 6/032; A61B 6/461; A61B 6/467; A61B 6/504; A61B 6/5205; G06T 11/005
See application file for complete search history.

(56) References Cited

U.S. PATENT DOCUMENTS

2004/0136491 A1 7/2004 Iatrou et al.
2008/0144764 A1* 6/2008 Nishide ................ A61B 6/4035
378/5

FOREIGN PATENT DOCUMENTS

JP 2005-533564 A 11/2005
JP 2008-154784 A 7/2008
(Continued)

OTHER PUBLICATIONS

Johnson et al "Material Differentiation by dual energy CT:initial experience" EUR Radiol 2007.*
(Continued)

*Primary Examiner* — Kim Vu
*Assistant Examiner* — Molly Delaney
(74) *Attorney, Agent, or Firm* — Mattingly & Malur, PC

(57) ABSTRACT

The present invention is capable of distinguishing four types or more of substances such as air, water (soft tissues), contrast medium, and bones (calcification) to diagnose progress of atherosclerotic sites using dual energy imaging. A subject is imaged with two types of different tube voltages and an image obtained by image reconstruction is binarized to carry out a reprojection process; thereby, the distance of penetration of air is estimated, the contribution of air in measurement projection data is determined, and the amount of reduction by the air is deducted from the projection data so as to enable distinction between four or more substances such as air, water (soft tissues), contrast medium, and bones (calcification).

13 Claims, 7 Drawing Sheets

(51) Int. Cl.
*A61B 6/03* (2006.01)
*G06T 11/00* (2006.01)
(52) U.S. Cl.
CPC ............ *A61B 6/504* (2013.01); *A61B 6/5205* (2013.01); *G06T 11/005* (2013.01); *A61B 6/481* (2013.01); *G06T 2207/10081* (2013.01); *G06T 2211/408* (2013.01)

(56) References Cited

FOREIGN PATENT DOCUMENTS

JP  2010-075443 A  4/2010
WO  WO 2012147004 A1 * 11/2012 ........... G06T 11/005

OTHER PUBLICATIONS

W. A. Kalender, et al. Evaluation of a prototype dual-energy computed tomographic apparatus, I. Phantom Studies Medical Physics, May/Jun. 1980, pp. 334-339, vol. 13, No. 3.

J. R. Vetter et al.,Evaluation of prototype dual-energy computed tomographic apparatus, II. Determination of vertebral bone mineral content. Medical Physics, May/Jun. 1980, pp. 340-343, vol. 13, No. 3.

International Search Report of PCT/JP2014/062134.

* cited by examiner

AIR EQUIVALENT IMAGE

WATER EQUIVALENT IMAGE

CONTRAST MEDIUM EQUIVALENT IMAGE

BONE EQUIVALENT IMAGE

⇩ COMPOSITION

X-RAY CT DEVICE AND PROCESSING METHOD

TECHNICAL FIELD

The present invention relates to an X-ray CT device, and more particularly, to the technique for imaging a subject by means of different types of energies, and processing the image.

BACKGROUND ART

The X-ray CT (Computed Tomography) device including an X-ray source for irradiating the subject with X-ray, and an X-ray detector located opposite the X-ray source for detecting the X-ray penetrating through the subject is configured to reconstruct the difference in the X-ray attenuation rate inside of the subject as an image by the data processing system based on projection data in a plurality of directions derived from rotary imaging of the area surrounding the subject. Generally, the X-ray tube is employed as the X-ray source, which irradiates the electrode with electron accelerated at high voltage for emitting the X-ray through bremsstrahlung phenomenon. In order to pick up the image over a wide range at higher speeds at a time, the X-ray detector is configured by arranging the X-ray detection elements each formed as the combination of scintillator and photodiode in a two-dimensional array.

The dual energy imaging method as one of methods for imaging the subject using a plurality of different energies is the technique for obtaining the substance composition information utilizing energy dependency of the X-ray attenuation coefficient by imaging the same subject at two types of tube voltages.

CITATION LIST

Patent Literature

PTL 1: Japanese Unexamined Patent Application Publication (Translation of PCT Application) No. 2005-533564

Nonpatent Literature

NPTL 1: W. A. Kalender, et. al., "Evaluation of a prototype dual-energy computed tomographic apparatus. I. Phantom studies." Med Phys. 13(3), 334-9, (1986)

NPTL 2: W. A. Kalender, et. al., "Evaluation of a prototype dual-energy computed tomographic apparatus. II. Determination of vertebral bone mineral content." Med Phys, 13(3), 340-3, (1986)

SUMMARY OF INVENTION

Technical Problem

The dual energy imaging method as disclosed in Nonpatent Literatures 1 and 2 allows three-type substance distinction. Diagnosis of progress of atherosclerotic sites requires distinction between calcification and the contrast medium or the stent. In order to satisfy the aforementioned requirement, it is necessary to distinguish among four types or more of substances such as air, water (soft tissues), contrast medium, and bone (calcification). Generally, the distinction among four types or more of substances further requires development of new hardware such as a multilayer detector and a photon counting detector, thus causing increase in the cost for the device.

It is an object of the present invention to provide an X-ray CT device and a processing method, which allow highly accurate distinction among four types or more of substances without requiring newly developed hardware.

Solution to Problem

The aforementioned object is accomplished by providing the X-ray CT device which includes a data collection section for imaging a subject with N different types of energy distributions so as to obtain the N types of projection data, and an imaging control section for converting the obtained N types of projection data into N+1 types of reference substance penetration distance data which are reconstructed to obtain reference substance equivalent tomographic images. The imaging control section obtains the penetration distance data of a substance {A} contained in the N+1 types of reference substances by executing p-value conversion of an image G reconstructed using the N types of projection data for reprojection, determining a contribution of the substance {A} in the N types of projection data using the obtained penetration distance data for removing the contribution, and converting the projection data after removal into the penetration distance data for image reconstruction so as to obtain N+1 types of reference substance equivalent tomographic images M1.

The aforementioned object is accomplished by the present invention providing the processing method of projection data using a processing section of the X-ray CT device, which executes p-value conversion of an image G reconstructed using N types of projection data obtained by imaging a subject with N different types of energy distributions for reprojection so as to obtain penetration distance data of a substance {A} contained in N+1 types of the reference substances, determines a contribution of the substance {A} in the N types of projection data using the obtained penetration distance data for removing the contribution, and converts the projection data after removal into the penetration distance data for image reconstruction so as to obtain N+1 types of reference substance equivalent tomographic images M1.

Advantageous Effects of Invention

The X-ray CT device provided as described above allows highly accurate distinction among four types or more of substances without requiring development of hardware such as the multilayer detector and the photon counting detector.

DESCRIPTION OF EMBODIMENTS

Figure 1A:
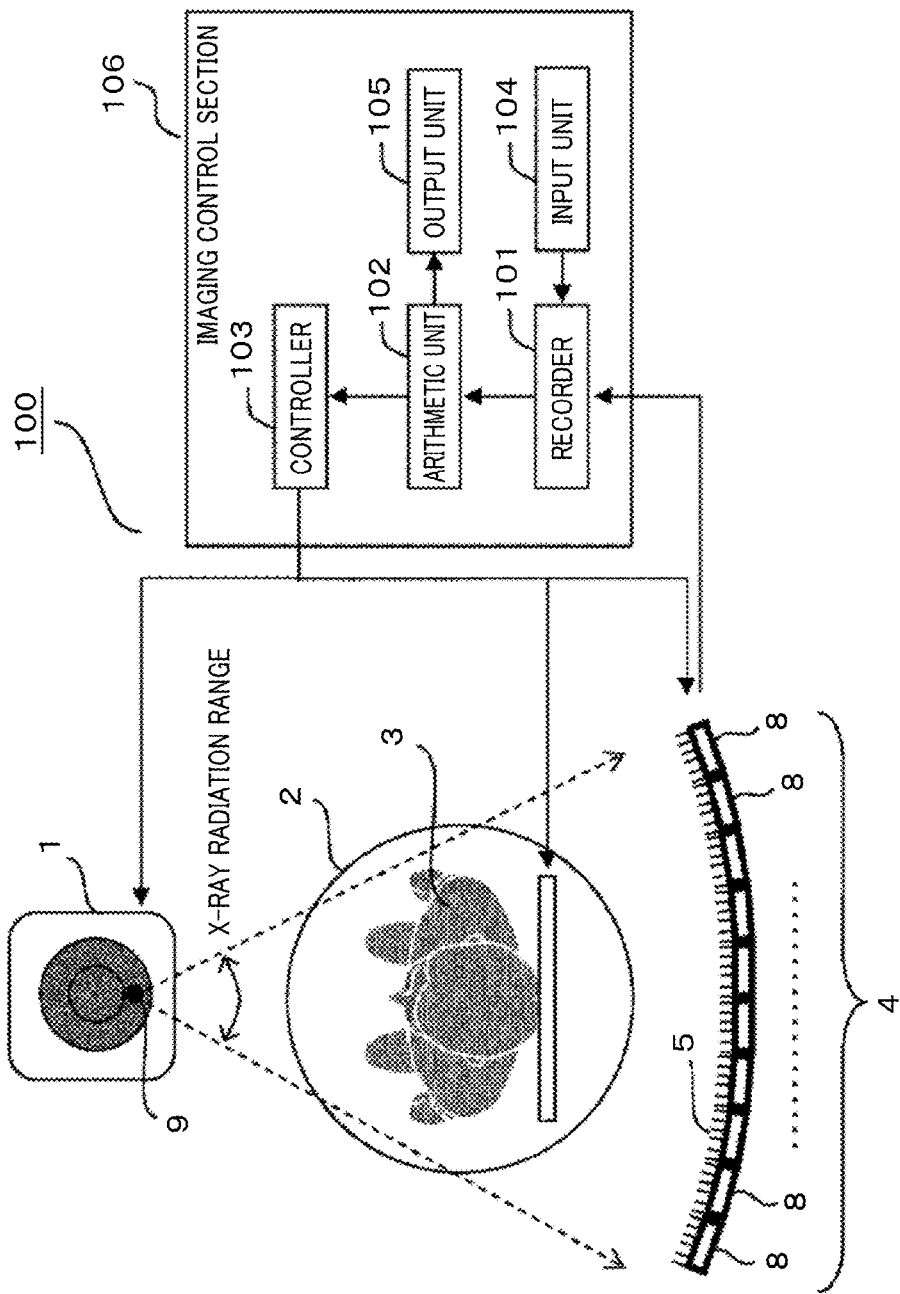
FIG. 1A is a schematic view representing a structure of an X-ray CT device according to a first embodiment, seen from an axial direction.

The embodiments according to the present invention will be described referring to the drawings. In the following description, the dual energy imaging method will be explained by exemplifying N different types (N=2) of energies. The number of energy types is not limited to the example as described above. The present invention is applicable to the case where the number N is set to three or more.

First Embodiment

The first embodiment relates to the X-ray CT device and the imaging method thereof.

The X-ray CT device according to the embodiment includes data collection sections 1, 4 for imaging a subject with N different types of energy distributions so as to obtain the N types of projection data, and an imaging control section 106 for converting the obtained N types of projection data into N+1 types of reference substance penetration distance data which are reconstructed to obtain reference substance equivalent tomographic images. The imaging control section 106 obtains the penetration distance data of p−1 types of substances $A_1, A_2, \ldots, A_{p-1}$ (hereinafter referred to as $\{A\}$) contained in the N+1 types of reference substances by executing p-value conversion of an image G reconstructed using the N types of projection data, determining a contribution of the substance $\{A\}$ in the N types of projection data using the obtained penetration distance data for removing the projection data after determination, and converting the projection data after removal into the penetration distance data for image reconstruction so as to obtain N+1 types of reference substance equivalent tomographic images M1.

In the processing method of projection data executed by a processing section 107 of the X-ray CT device according to the embodiment, the processing section 107 executes p-value conversion of an image G reconstructed using N types of projection data obtained by imaging a subject with N different types of energy distributions for reprojection so as to obtain penetration distance data of p−1 types of substance $\{A\}$ contained in N+1 types of the reference substances, determines a contribution of the substance $\{A\}$ in the N types of projection data using the obtained penetration distance data for removing the projection data after determination, and converts the projection data after removal into the penetration distance data for image reconstruction so as to obtain N+1 types of reference substance equivalent tomographic images M1.

The following description will be made by exemplifying conditions of N=2, p=2, the substance $\{A\}$=air as a single type. However, it is not limited to the aforementioned example.

A structure example of the X-ray CT device according to the first embodiment will be described referring to FIGS. 1A and 1B. FIG. 1A is a view representing the structure of an X-ray CT device 100 according to the embodiment seen from the axial direction. An aperture 2 is formed in the center of a not shown gantry of the X-ray CT device 100, which allows entry of a subject 3. A scanner of the X-ray CT device 100 is provided with an X-ray tube 1 as the X-ray source, and an X-ray detector 4, both of which are rotatably supported with the gantry, taking the center of the aperture 2 as a rotary center axis. The aforementioned structure makes it possible to allow rotation imaging of the subject 3 in the aperture 2.

The X-ray tube 1 has a finite-sized X-ray focus 9 therein for emitting X-ray. The X-ray detector 4 is disposed opposite the X-ray tube 1 having the subject 3 interposed therebetween. The X-ray detector 4 may be divided into a plurality of detector modules 8. The respective detector modules 8 are arranged into an arc shape or a flat panel shape while having the X-ray focus 9 as the center. The detector modules 8 are provided with scattered X-ray prevention grids 5 at the side facing the X-ray tube 1 in order to remove the scattered X-ray generated by the subject 3. The X-ray tube 1 and the X-ray detector 4 employed for the purpose of at least two types of projection data will be collectively referred to as a data collection section for collecting projection data in the specification.

The control of imaging the subject 3 in the X-ray CT device 100 for data collection is carried out by a controller 103 by means of a recorder 101 and an arithmetic unit 102 based on the scan condition set by the user via an input unit 104. Multiple projection data derived from the data collection sections 1, 4 through the rotation imaging controlled by the controller 103 are recorded in the recorder 101. Then the arithmetic unit 102 carries out arithmetic image processing so that an output unit 105 displays such information as tomographic image of the subject 3.

Figure 1B:
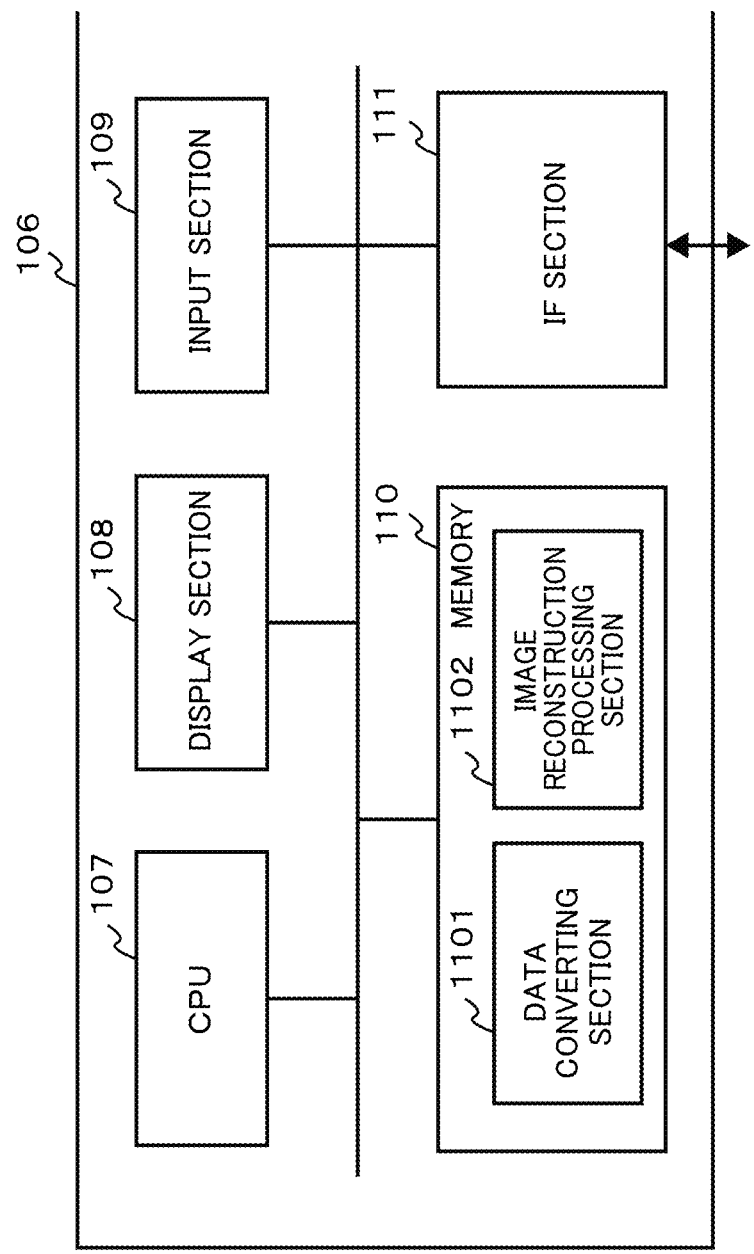
FIG. 1B is a block diagram of an imaging control section of the X-ray CT device according to the first embodiment.

Referring to the block diagram shown in FIG. 1B, an imaging control section 106 of the X-ray CT device 100 includes the recorder 101, the arithmetic unit 102, the controller 103, the input unit 104, and the output unit 105. The imaging control section may be configured as a computer having an inner bus connecting a processing section such as Central Processing Unit (CPU) 107, a storage section including the memory 110 and the hard disk drive (HDD) for storing various types of processing programs such as the data converting section and the image reconstruction processing section, which are executed by the CPU 107, a display section 108 such as the display, an input section 109 such as a keyboard, and an interface (IF) section 111 to which the projection data are input.

In other words, the imaging control section 106 includes the interface section to which N types of projection data are input, the processing section for processing the N types of projection data, and the storage section for storing the data converting section and the image reconstruction processing section which are executed by the processing section.

In other words, the X-ray CT device of the embodiment is configured that the processing section 107 constituted by the CPU executes the predetermined function programs, for example, the data converting section 1101 for data converting process and the image reconstruction processing section 1102 for image reconstruction processing, which are stored in the memory 110 with respect to the projection data derived from the detector modules 8 via the IF section 111 and stored in the storage section such as the memory 110 based on the set scan condition. The processing section 107 executes the predetermined programs to realize functions of the arithmetic unit 102, and further the controller 103 as shown in FIG. 1A so as to display the resultant tomographic image on the display section 108.

Various methods have been proposed for obtaining the projection data set of the subject based on N types, that is, two types of energy distributions. For example, there have been disclosed the dual rotation method for imaging twice each at different tube voltage, the fast kV switching method for imaging by switching the tube voltage at high speeds during the single rotation, the dual layer detector method using a dual layer detector, allowing the upper layer to measure the X-ray in the low energy distribution, and the lower layer to measure the X-ray in the high energy distribution, dual source method for disposing two pairs of tube and detector in the gantry to set the tube voltages of the tube to different values, the photon counting method for measuring the X-ray energy by measuring the X-ray per photon, and the method for alternately arranging detection elements each with different energy sensitivity on the two-dimensional array. The structure according to this embodiment does not depend on the aforementioned data acquiring method. In the following description of the embodiment, the dual energy imaging method will be explained by exemplifying the use of dual rotation type for imaging twice each at the different tube voltage by setting the low tube voltage to 80 kV, and the high tube voltage to 140 kV.

The description will be made with respect to the basic principle of the dual energy imaging method of reference substance resolution type for the X-ray CT device according to the embodiment.

The output I at each detection element is expressed by the following formula (1), where S denotes an initial X-ray spectrum, $\varepsilon$ denotes the X-ray energy, $\eta$ denotes efficiency, $\mu$ denotes a mass attenuation coefficient, Z denotes an atomic number, s denotes an X-ray path, and $\rho$ denotes a substance density.

[Formula 1]

$$I=\int S(\varepsilon)\varepsilon\eta(\varepsilon)Exp[-\int\mu(\varepsilon,Z(s),s)\rho(s)ds]d\varepsilon \quad (1)$$

It is assumed that the mass attenuation coefficient is decomposed into N+1 types, that is, three reference substances, for example, air (AIR), water ($H_2O$), and iodine contrast medium (I) as formula (2) expresses. Substitution of those values in the formula (1) results in the formula (3). For simplicity, the efficiency n is set to 1.

[Formula 2]

$$\int\mu(\varepsilon,Z)\rho(s)ds \approx \mu_{AIR}\rho_{AIR}s_{AIR}+\mu_{H2O}\rho_{H2O}s_{H2O}+\mu_I\rho_I s_I \quad (2)$$

[Formula 3]

$$I(s_{AIR},s_{H2O},s_I)=\int S(\varepsilon)\varepsilon Exp[-\mu_{AIR}\rho_{AIR}s_{AIR}-\mu_{H2O}\rho_{H2O}s_{H2O}-\mu_I\rho_I s_I]d\varepsilon \quad (3)$$

Upon substitution of the theoretical value on the assumption that the mass attenuation coefficient $\mu_i$ and the density $\rho_i$ of the reference substance (hereinafter expressed with the suffix i), and incident spectrum S are known, the detection element output I may be considered as being function only of the penetration distance $s_i$. The representative value is used for the density, and variation in the density will be temporarily replaced with variation in the distance.

The imaging system of the X-ray CT device is configured that the distance from the X-ray focus 9 to each of the detection elements of the X-ray detector 4 is set to a constant value L so that the output I of the formula (3) becomes substantially the function of two variables of $S_{H2O}$ and $S_I$.

Generally, besides the value I, the output value J after sensitivity calibration (air calibration) and logarithmic transformation as expressed by the formula (4) will be used as the output to the reconstruction system of the X-ray CT device.

The Gain denotes the appropriate constant, and $I_o$ denotes the detector output (=air data) with no subject.

[Formula 4]

$$J=-Gain \times Log_{10}(I/I_0) \quad (4)$$

It is assumed that outputs after the logarithmic transformation at high/low tube voltages corresponding to two different types of energies are set to $J_H$ and $J_L$. Dependency of the reference substance penetration distance $s_i$ may be preliminarily calculated numerically. The calculated value is compiled into database so as to be stored in the memory as the storage section.

The reference substance penetration distance $s_i$ is derived from the experimental value by searching the combination of $s_i$ values for minimizing the square of difference between the experimental values $J_L^{exp}$, $J_H^{exp}$, and the calculated theoretical values $J_L^{ideal}$, $J_H^{ideal}$ from the database. The aforementioned processing will be referred to as penetration distance conversion in the specification hereinafter.

[Formula 5]

$$min \chi^2(s_i), \chi^2(s_i) \equiv (J_L^{exp}-J_L^{ideal}(s_i))^2 + (J_H^{exp}-J_H^{ideal}(s_i))^2 \quad (5)$$

The obtained reference substance penetration distance $s_i$ is converted into the dimension of density×length through the formula (6) so that the respective images are reconstructed for providing the reference substance equivalent images.

[Formula 6]

$$J_i=Gain_i \times \rho_i s_i \quad (6)$$

The aforementioned reference substance distinction method allows clear separation of the respective reference substances from one another in terms of image. It also allows removal of beam hardening artifacts for the purpose of generating the image in consideration of energy.

Based on the same information, it is also possible to provide the virtual standard kV image, the virtual single energy image, the effective atomic number image, the electron density image, the interaction weighted image and the like in addition to the reference substance equivalent image.

The method of distinguishing among four types of reference substances with the structure of the embodiment will be described.

Referring to the formula (7), the attenuation coefficient is divided into four reference substances (for example, air (AIR), water ($H_2O$), iodine contrast medium (I), and bone (Bone)). They are substituted in the formula (1), and the efficiency $\eta$ is set to 1 to provide the formula (8).

[Formula 7]

$$\int\mu(\varepsilon,Z)\rho(s)ds \approx \mu_{AIR}\rho_{AIR}s_{AIR}+\mu_{H2O}\rho_{H2O}s_{H2O}+\mu_I\rho_I s_I+\mu_{Bone}\rho_{Bone}s_{Bone} \quad (7)$$

[Formula 8]

$$I(s_{AIR},s_{H2O},s_I,s_{Bone})=\int S(\varepsilon)\varepsilon Exp[-\mu_{AIR}\rho_{AIR}s_{AIR}-\mu_{H2O}\rho_{H2O}s_{H2O}-\mu_I\rho_I s_I-\mu_{Bone}\rho_{Bone}s_{Bone}]d\varepsilon \quad (8)$$

As described above, the detection element output I may be regarded as the function only of the reference substance penetration distance $s_i$, it is possible to preliminarily calculate the reference substance penetration distance dependency database for outputs. As described above, the total of reference substance penetration distance values agrees with the distance L between the focus and the detection element ($\Sigma_i s_i=L$). Accordingly, it is clear that the detection element output is a substantial function of three variables of $S_{H2O}$, $S_I$, $S_{Bone}$. However, because of less constraint condition for variables, use of the penetration distance conversion with least squares method may fail to provide the unique combinations of the reference substance penetration distance values for reproducing the high/low tube voltage outputs.

Concerning the X-ray CT device and processing method according to the embodiment, the air penetration distance $S_{AIR}$ will be obtained by performing any one of two methods as described below.

Figure 2:
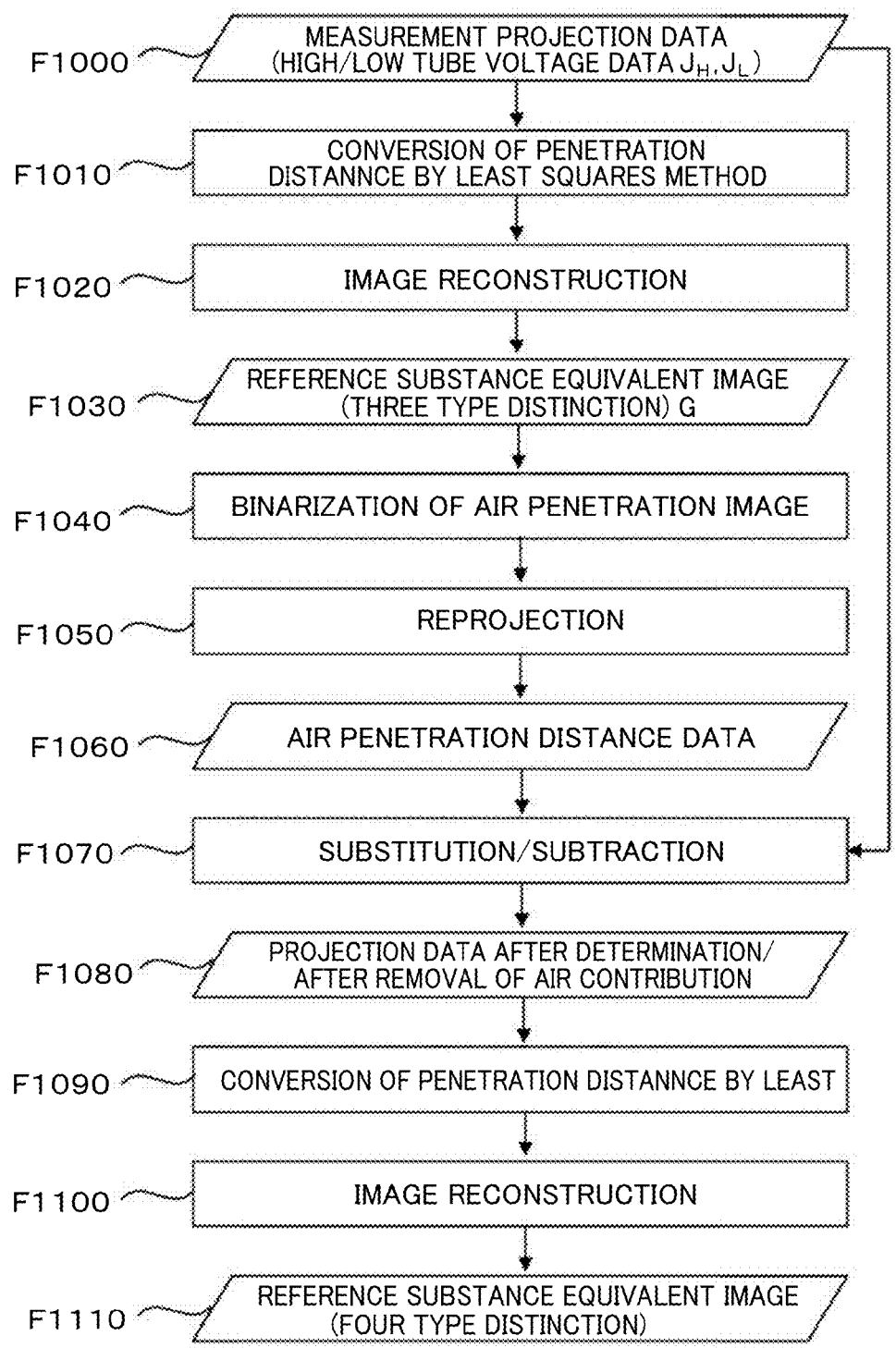
FIG. 2 is a flowchart representing an example of the data processing flow according to the first embodiment.
Figure 3:
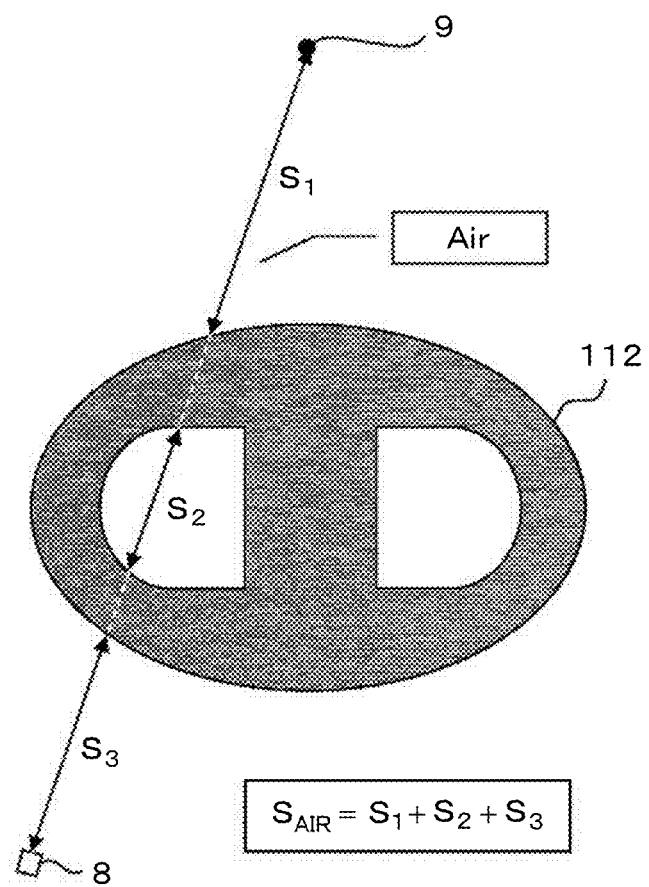
FIG. 3 is a schematic view representing the method of estimating the air penetration distance according to the first embodiment.

FIG. 2 is a flowchart of the arithmetic process executed by the processing section 107 constituted by the CPU of the X-ray CT device shown in FIG. 1B in accordance with a first method of the embodiment. FIG. 3 schematically represents how the air penetration distance is obtained. Referring to the drawing, a sign 112 schematically represents the subject 3 shown in FIG. 1A. As the drawing shows, the air penetration distance is expressed by $s_{AIR}=(S_1+S_2+S_3)$.

As described above, the arithmetic process executed in the X-ray CT device as shown in FIG. 1B is mainly divided into the data converting process and the image reconstruction process, both of which will be realized through execution of the data converting section 1101 and the image reconstruction processing section 1102 stored in the memory 110 by the processing section 107 constituted by the CPU. For simplifying the explanation, the description with respect to the process to be executed will be made on the assumption that such process is executed by the processing section 107 constituted by the CPU without identifying the specific processing section whether the data converting section 1101 or the image reconstruction section 1102. This applies to the description with respect to the second method, which will be explained later.

<First Method>

With the first method, the imaging control section 106 executes penetration distance conversion through the least squares method using the N types of measurement projection data for image reconstruction so that N+1 types of reference substance equivalent images G are obtained. Among those images, the image of the substance {A} is binarized for reprojection to obtain the penetration distance data of the substance {A} contained in the N+1 types of reference substances. The contribution of the substance {A} in the N types of projection data is determined using the penetration distance data of the obtained substance {A} so as to be substituted and subtracted for removal. The projection data after removal is converted into the penetration distance data through the penetration distance conversion. Then the image reconstruction is executed to obtain the reference substance equivalent tomographic images of (N+1)-type distinction. In other words, the first method converts the N types of measurement projection data into the penetration distance data of N+1 types of reference substances, which will be subjected to the image reconstruction to obtain the reference substance equivalent tomographic image as the image G. The following is the explanation under the conditions of N=2, p=2, the substance {A}=air as the single type.

Referring to FIG. 2, likewise the reference substance distinction method for three types of reference substances as described above, the measurement projection data (F1000) are subjected to penetration distance conversion with the least squares method (F1010) for image reconstruction (F1020) to obtain three-type distinction reference substance equivalent images G (F1030). Especially, the air penetration image among those images is binarized (F1040) to reproject the image (F1050) so that the length of the part other than the air is obtained. The calculated length is subtracted from the focus-detection element distance L to obtain the air penetration distance $s_{AIR}$ (F1060).

The reprojection process (F1050) is also referred to as the forward projection process for obtaining the projection data (sinogram) from the image, which is the reverse process of the image reconstruction.

The obtained air penetration distance $s_{AIR}$ is substituted in the formula (8) (F1070) to provide projection data (F1080) after determination of air contribution. It is also possible to remove the air contribution from both sides of the formula (8). In either case, the air contribution contained in the attenuation ratio of the signal as the output is determined.

As described above, since dependency of the detection element output on the reference substance penetration distance $s_i$ becomes two-variable function, the remaining values of the reference substance penetration distance $s_i$ may be obtained by executing the penetration distance conversion (F1090) with the least squares method.

Figure 4:
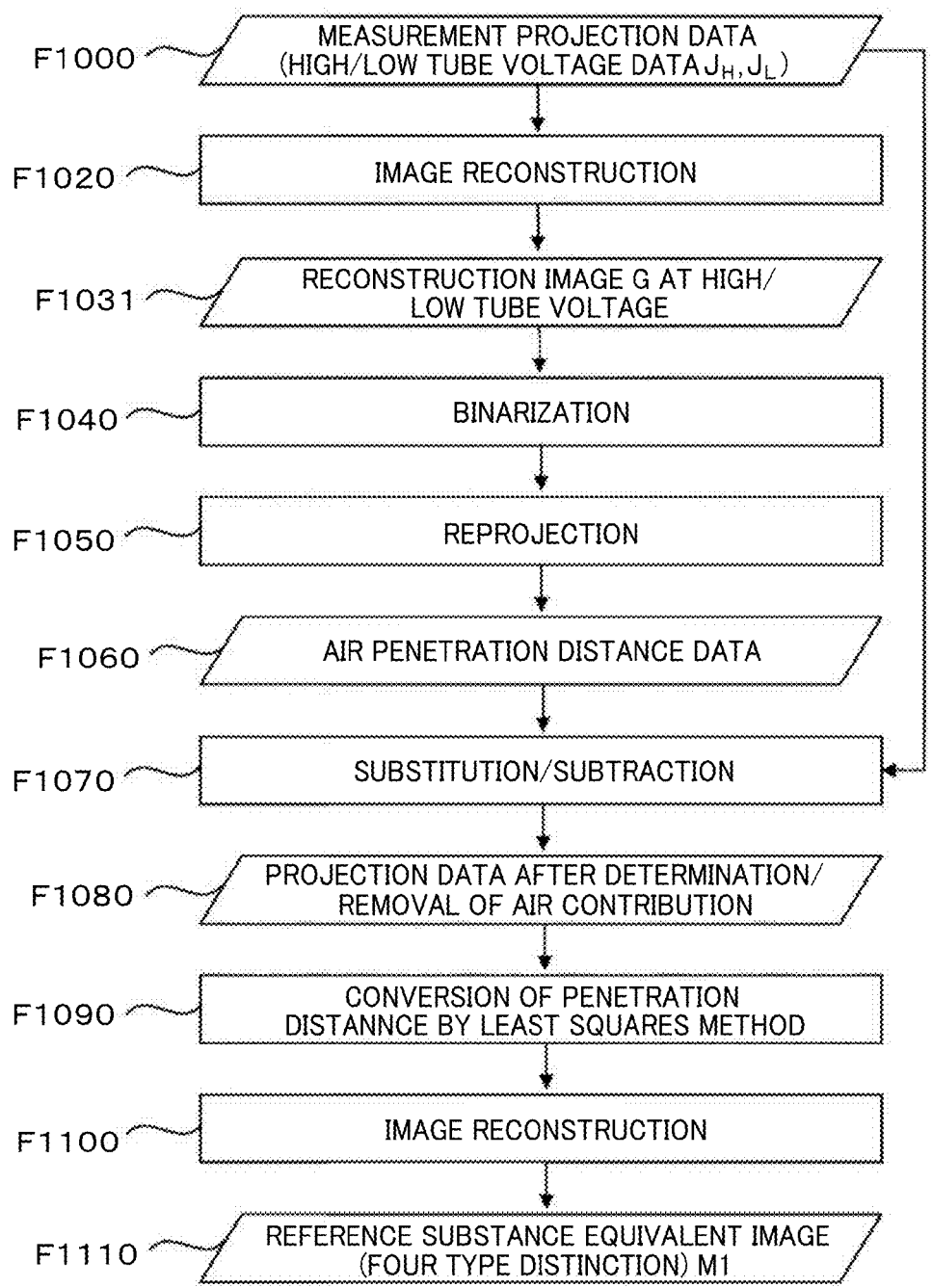
FIG. 4 is a flowchart representing another example of the data processing flow according to the first embodiment.

FIG. 4 represents the flowchart of the process according to the second method of the embodiment. As described above, the following process is realized by execution of the data converting section 1101 and the image reconstruction processing section 1102 stored in the memory 110 by the CPU 107.

<Second Method>

With the second method, the imaging control section 106 binarizes the image G reconstructed using at least one type of projection data among those of N types for reprojection so as to obtain the penetration distance data of the substance {A} contained in the N+1 types of reference substances. Using the penetration distance data of the obtained substance {A}, contribution of the substance {A} in the N types of projection data is determined and subtracted for removal. The projection data after removal are converted into the penetration distance data through the penetration distance conversion. The converted data are image reconstructed to obtain the (N+1)-type distinction reference substance equivalent images. In other words, the second method uses the image derived from image reconstruction of at least one type of projection data among those of N types as the image G. The following explanation will be made by exemplifying the conditions of N=2, p=2, the substance {A}=air as the single type.

Referring to FIG. 4, among high/low tube voltage reconstruction images (F1031) G derived from subjecting the measured projection data (F1000) to image reconstruction (F1020), the image with less false image, for example, the high tube voltage image is binarized (F1040) using the CT value-500 HU as the threshold. The binarized image is reprojected (F1050) to obtain the length of the part other than the air, which is subtracted from the focus-detection element distance L for calculating the air penetration distance $s_{AIR}$ (F1060). Likewise FIG. 2, the obtained air penetration distance $s_{AIR}$ is substituted in the formula (8) (F1070) so as to obtain the projection data (F1080) after determination of the air contribution. The subsequent process steps (F1090-F1110) such as the penetration distance conversion are the same as those of the first method, and explanations thereof, thus will be omitted.

It is possible to perform distinction of five or more types of substances by repeating the aforementioned process steps. For example, the processing section 107 constituted by the CPU in the imaging control section 106 executes q-value conversion of a reference substance equivalent tomographic image M1 with respect to substances $B_1, B_2, \ldots B_{q-1}$ contained in N+1 types of the reference substances (hereinafter referred to as {B}) which are different from the substance {A}, and determines respective contributions of the substances {A} and {B} in N types of projection data using the reprojected data. It is therefore possible to distinguish among five or more types of substances by obtaining N+1 types of reference substance equivalent tomographic images M2 different from those of the substances {A} and {B}.

In other words, the imaging control section 106 of the X-ray CT device according to the embodiment is configured to execute the q-value conversion of the reference substance equivalent image M1 with respect to the substance {B} contained in the N+1 types of reference substances, which is different from the substance {A}, and determines respective contributions of the substances {A} and {B} in N types of projection data using the reprojected penetration distance data so as to obtain the N+1 types of reference substance equivalent tomographic images M2, which are different from those of the substances {A} and {B}.

Likewise the binarization (F1040), it is possible to directly distinguish among the p+2 types, namely, five types of substances by executing the p-value conversion, for example, ternarization through selection of the appropriate threshold in accordance with the substance.

However, the substances {A} and {B} which allow accurate acquisition of the penetration distance from those substance images through reprojection process are limited to those with known density values, and estimated to be kept substantially constant in the imaging region.

Figure 5:
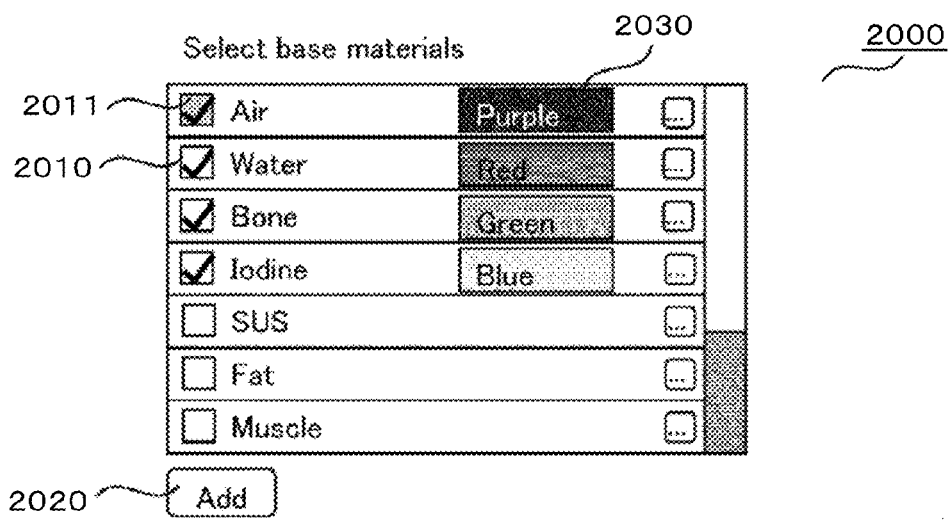
FIG. 5 is a view representing an example of a user interface used for selecting a reference substance according to the first embodiment.

FIG. 5 illustrates an example of an input display of parameters required for realizing the X-ray CT device and the processing method according to the embodiment. The input data may be displayed as GUI (Graphical User Interface) on the display of the output unit 105 shown in FIG. 1A, the input section 109 shown in FIG. 1B, or the display section 108 serving as the input section. The substance regarded as being highly used is preliminarily defined, and displayed in a list 2000 on the GUI screen.

Figure 6:
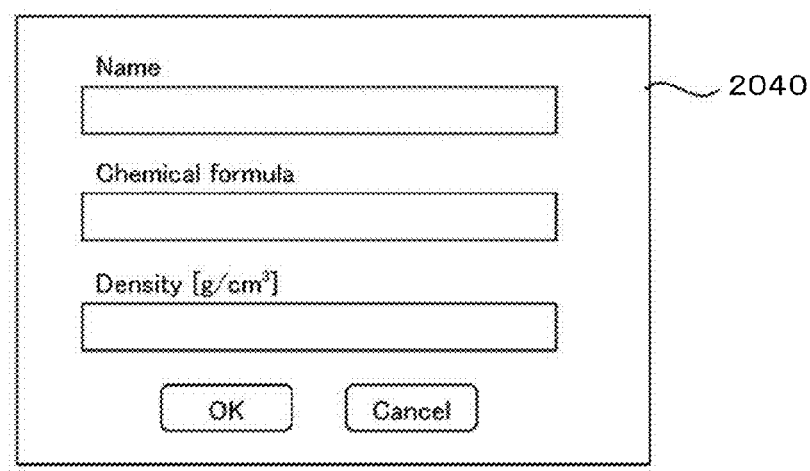
FIG. 6 is a view representing another example of the user interface for adding the reference substance according to the first embodiment.

It is possible to add the user-defined substance to the list 2000 by inputting the name, chemical formula, and density of the substance by a button 2020 via a dialog 2040 as shown in FIG. 6. The user is allowed to select the arbitrary reference substance from the list 2000 via a check box 2010. As described above, the X-ray CT device of the embodiment includes the input section which allows the user to arbitrarily set the reference substance and the substance {A} such as air.

Referring to FIG. 5, a shaded section 2011 of the check box clearly shows that the air (Air) is the substance subjected to reprojection of the reconstruction image and calculation of the penetration distance. Upon selection of four or more types of the reference substances, the corresponding section will be automatically shaded sequentially from the one that has been firstly checked. The general CT image is displayed while setting the CT value as brightness. Meanwhile, the reference substance equivalent image according to the embodiment is displayed, taking density (amount proportional to the density) of the reference substance as brightness.

Figure 7:
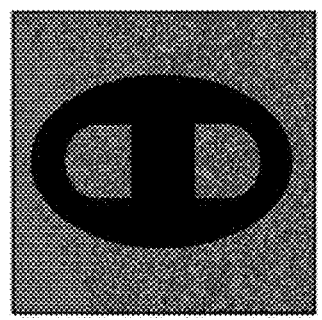
FIG. 7 is a view representing an example of a color image derived from composition of equivalent images of reference substances according to the first embodiment.
Figure 7:
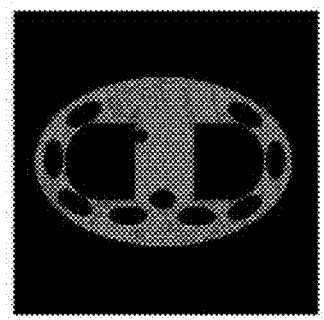
Figure 7:
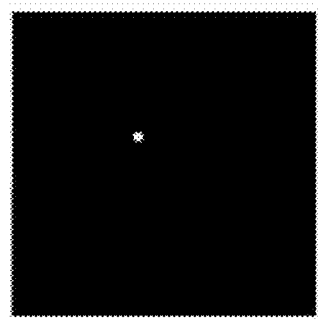
Figure 7:
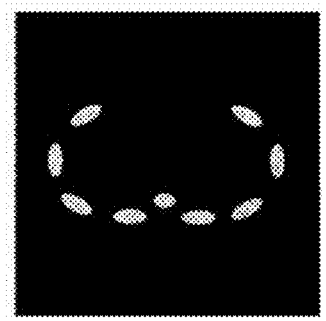
Figure 7:
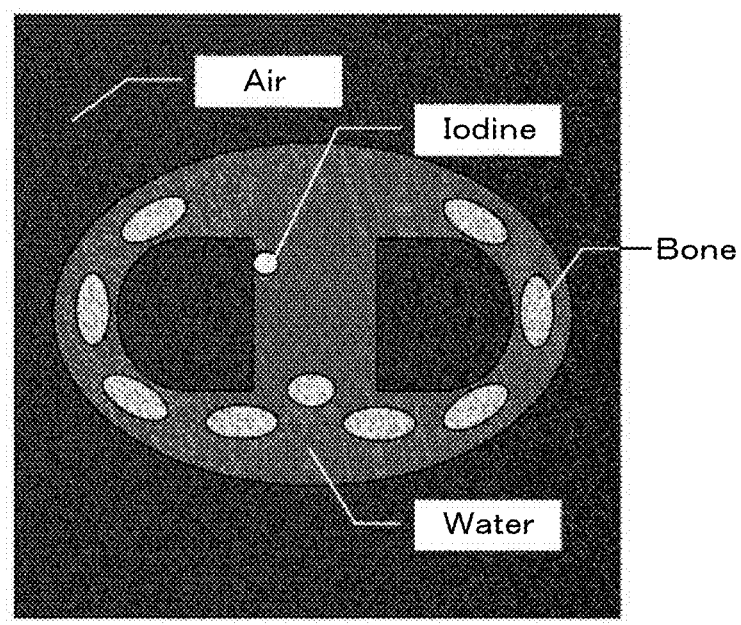

Referring to FIG. 7 indicating an example of the display, appropriate colors (for example, purple, red, green, blue) are allocated to the respective reference substances such as air (Air), water (Water), contrast medium (Iodine), and bone (Bone) to generate monotonized images. The colors of the respective pixels displayed at the upper section are composited and displayed so as to allow display of the density information of four types of reference substances collectively on the single color image. For graphical convenience, difference in the density (brightness) is omitted in FIG. 7.

Upon selection of the reference substance by the user on the GUI screen of the output unit 105 as shown in FIG. 5, a button 2030 is automatically colored in accordance with the check state of the check box 2010, and displayed for the user. The user is allowed to change the color via the button 2030, or allowed to set the colorless mode (not displayed in overlapped manner).

Specifically, the imaging control section 106 of the X-ray CT device according to the embodiment has the display section capable of displaying the reference substance equivalent tomographic image M1. The imaging control section 106 includes the display section capable of displaying the reference substance equivalent tomographic image M1, and allows setting of arbitrary colors to be allocated to the reference substance and the substance {A} displayed on the display section from the input section. The imaging control section 106 generates the monotonized images in the colors set to be allocated to the reference substance and the substance {A}, and displays the composite color image on the display section.

The present invention includes various modified examples without being limited to the embodiment as described above. The above embodiment has been described in detail for better understanding of the present invention, and is not limited to the one provided with all the components as described in the embodiment. It is also possible to replace a part of the structure of the embodiment with the one of another embodiment, and add the structure of the embodiment to that of another one. It is further possible to have the part of the structure of the respective embodiments added to, removed from and replaced with the other structure.

The description has been made by exemplifying that a part or all of the structures, functions and processing section may be realized by the program. A part or all of them may be realized by means of hardware, for example, designed with the integrated circuit.

LIST OF REFERENCE SIGNS

1 X-ray tube (X-ray source)
2 aperture
3 subject
4 X-ray detector
5 scattered X-ray prevention grid
8 detector module
9 X-ray focus
100 X-ray CT device
101 storage unit
102 arithmetic unit
103 controller
104 input unit
105 output unit
106 imaging control section
112 subject

The invention claimed is:

1. An X-ray CT (Computed Tomography) device comprising:
a data collection section including at least an X-ray tube and an X-ray detector for imaging a subject with N different types of energy distributions so as to obtain N types of projection data; and
a processor programmed to:
convert the obtained N types of projection data into N+1 types of reference substance penetration distance data for N+1 types of reference substances which are reconstructed to obtain reference substance equivalent tomographic images, wherein the processor is further programmed to obtain the reference substance penetration distance data of a first substance contained in the N+1 types of reference substances by executing a p-value conversion of a first image reconstructed using the N types of projection data for reprojection, determining a contribution of the first substance in the N types of projection data using the obtained reference substance penetration distance data for removing the contribution, and converting the projection data after removing the contribution into the reference substance penetration distance data for image reconstruction so as to obtain N+1 types of reference substance equivalent tomographic images, and wherein the processor is further programmed to execute q-value conversion of one of the reference substance equivalent tomographic images with respect to a second substance contained in the N+1 types of reference substances, which is different from the first substance, and to determine contributions of the first and second substances in the N types of projection data using the reprojected reference substance penetration distance data so as to obtain the N+1 types of reference substance equivalent tomographic images which are different from the reference substance equivalent tomographic images of the first and second substances.

2. The X-ray CT device according to claim 1, wherein the processor is further programmed to set the reference substance equivalent tomographic images to the first image.

3. The X-ray CT device according to claim 1, wherein the processor is further programmed to set an image obtained by image reconstructing at least one type of projection data among the N types of projection data to the first image.

4. The X-ray CT device according to claim 1, wherein the first substance is air.

5. The X-ray CT device according to claim 1, wherein the processor is further programmed to receive a selection of the reference substances and the first substance.

6. The X-ray CT device according to claim 1, wherein the processor is further programmed to display the reference substance equivalent tomographic images.

7. The X-ray CT device according to claim 5, wherein the processor is further programmed to receive a selection of colors for the reference substances and the first substance, and to display the reference substance equivalent tomographic images with the reference substances and the first substance in the selected colors.

8. The X-ray CT device according to claim 6, wherein the processor is further programmed to generate monotonized reference substance equivalent tomographic images in colors respectively set for the reference substances and the first substance, and display a composite color reference substance equivalent tomographic image.

9. The X-ray CT device according to claim 1, further comprising:

a storage medium coupled to the processor and which stores the N types of projection data and the reference substance equivalent tomographic images.

10. An X-ray CT processing method, comprising:

imaging a subject with N different types of energy distributions with an X-ray tube and an X-ray detector so as to obtain N types of projection data;

executing a p-value conversion of a first image reconstructed using the N types of projection data for reprojection so as to obtain reference substance penetration distance data of a first substance contained in N +1 types of reference substances;

determininq a contribution of the first substance in the N types of projection data using the obtained reference substance penetration distance data for removing the contributions;

convertinq the N types of projection data after removal of the contribution into the reference substance penetration distance data for image reconstruction so as to obtain N+1 types of reference substance equivalent tomographic images;

executing a q-value conversion of the reference substance equivalent tomographic images with respect to a second substance contained in the N+1 types of reference substances, which is different from the first substance, and to determine contributions of the first and second substances in the N types of projection data using the reprojected reference substance penetration distance data so as to obtain the N+1 types of reference substance equivalent tomographic images which are different from the reference substance equivalent tomographic images of the first and second substances.

11. The X-ray CT processing method according to claim 10, further comprising:

setting the reference substance equivalent tomographic images to the first image.

12. The X-ray CT processing method according to claim 10, further comprising:

setting an image obtained by image reconstructing at least one type of projection data among the N types of projection data to the first image.

13. The X-ray CT processing method according to claim 10, wherein the first substance is air.

* * * * *